United States Patent [19]
Gutierrez et al.

[11] 3,992,414
[45] Nov. 16, 1976

[54] PROCESS FOR THE PREPARATION OF SELECTIVELY HALOGENATED KETALS

[75] Inventors: Eddie N. Gutierrez, Fort Lee; Robert C. Reardon, Jr., Tenafly, both of N.J.

[73] Assignee: Lever Brothers Company, New York, N.Y.

[22] Filed: Aug. 1, 1975

[21] Appl. No.: 601,105

Related U.S. Application Data

[62] Division of Ser. No. 426,855, Dec. 20, 1973, Pat. No. 3,919,328.

[52] U.S. Cl. .............................................. 260/340.9
[51] Int. Cl.² ........................................ C07D 317/10
[58] Field of Search ............... 260/340.9 R, 615 A, 260/340.9

[56] References Cited
UNITED STATES PATENTS

| | | | |
|---|---|---|---|
| 3,919,328 | 11/1975 | Gutierrez | 260/615 A |
| 3,944,568 | 3/1976 | Gutierrez et al. | 260/340.9 |

*Primary Examiner*—Ethel G. Love
*Attorney, Agent, or Firm*—James J. Farrell; Kenneth F. Dusyn; Melvin H. Kurtz

[57] ABSTRACT

A method is disclosed wherein selectively halogenated ketals and ultimately, halogenated ketones are prepared by treating secondary ethers with halogen in an organic solvent under conditions of ordinary temperature and pressure. This method obviates the need for extreme times, temperatures, and complex equipment.

8 Claims, No Drawings

PROCESS FOR THE PREPARATION OF SELECTIVELY HALOGENATED KETALS

This is a division, of application Ser. No. 426,855, filed Dec. 20, 1973, now U.S. Pat. No. 3,919,328.

BACKGROUND OF THE INVENTION

1. Field of the Invention

This invention pertains to a new and improved process for the preparation of selectively halogenated ketals and ketones from secondary ethers, more specifically selectively chlorinated or brominated ketals and ketones.

2. Description of the Prior Art

Heretofore, it has been extremely difficult to obtain selectively and symmetrically dihalogenated ketones and ketals from ethers. Deno et al (J. Am. Chem. Soc., Vol. 89, pp 3550–3554 (1967) disclose the oxidation of a wide variety of aliphatic ethers with aqueous bromine. The products generally obtained are carboxylic acids or ketones, depending upon whether the starting ether is primary or secondary. Bromination products appear when the reaction is conducted under strongly acidic conditions. The products, however, are of the monobrominated variety and the isomers are not easily separable, if at all. The separation of isomers aspect of this invention is considered to be an additional feature of the instant application.

DESCRIPTION OF THE INVENTION

This invention relates to a novel method for the preparation of selectively halogenated, more specifically selectively chlorinated or brominated ketals and ketones from secondary ethers. A specific embodiment of the instant invention relates to the preparation of selectively and symmetrically chlorinated or brominated ketals and ketones from said ethers. The instant process differs from processes known heretofore in that the reaction takes place in a solvent selected from monohydric and polyhydric alcohols at conditions of ordinary temperatures and pressure.

The method for preparing these halogenated derivatives may be illustrated as follows:

I. Synthesis from secondary ethers

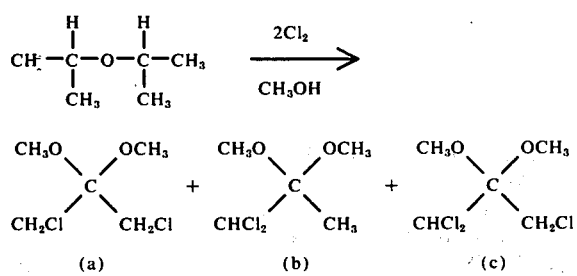

II. Synthesis from secondary methyl ether

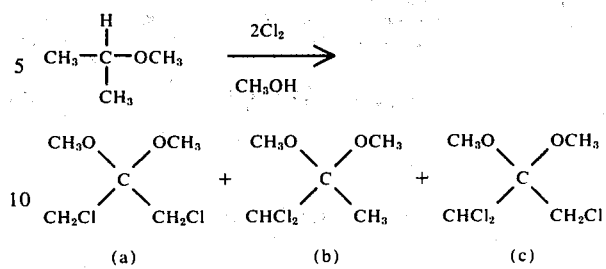

Separation of (a) and (b) or (c) in either of reactions I and II can be accomplished easily.

These chlorinated products may be hydrolyzed under acid conditions to produce chlorinated ketones. For example:

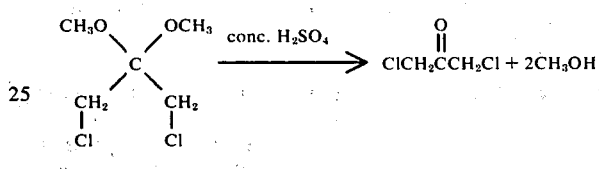

This method effects oxidative cleavage, chlorination and acetylation in one process.

Accordingly, it is an object of this invention to provide a method of preparing selectively halogenated ketals and ketones which comprises treating with a halogen selected from the group consisting of chlorine and bromine ether compounds of Formula I:

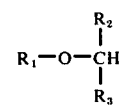

wherein $R_1$ is a straight chain unsubstituted alkyl of 1 to 20 carbon atoms, $R_2$ and $R_3$ are straight chain unsubstituted alkyl groups of from 1 to 10 carbon atoms; said treatment taking place in an organic solvent selected from the group consisting of monohydric and polyhydric alcohols wherein the ratio of said solvent to said ether is from about 5 to 1 to about 20 to 1 and at a temperature of from about 0° C to about 80° C.

Diisopropyl ether may be halogenated according to the process of the instant invention.

It is a further object of the invention to obtain increased yields of selectively and symmetrically dihalogenated products which are easily separable from other isomeric reaction products.

It is also an object of this invention to provide a more economical and feasible method for the preparation of compounds which find use as fungicides, fiber treatment agents, resinification agents in the formation of resinous aromatic hydrocarbons, pesticides and plasticizers.

The novel process of the instant invention may be exemplified as follows:

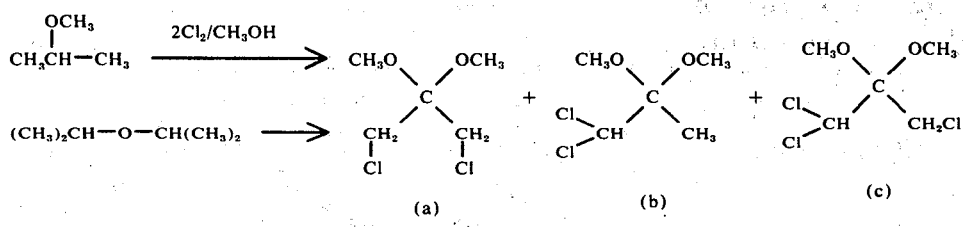

(a) can easily be separated from (b) and/or (c).

The method of the present invention is conveniently carried out by slowly bubbling halogen through an alcoholic solution of the ether at room temperature and atmospheric pressure. The method requires no special apparatus. All that is required is control of the halogen being introduced and stirring. The reaction yields halogenated ketals which can be easily separated from one another.

The oxidation/halogenation of ethers in alcohol differs from previous oxidation/halogenation of ethers in water in that in the former, halogenated ketals are formed which are easily separable while in water halogenated ketones are formed which are difficultly separable.

An additional advantage of this method over prior art is that the latter discloses no means of producing dihalogenated or trihalogenated ketals from ethers in a one step process.

The oxidative cleavage occurs under anhydrous conditions and it is believed that the methyl hypohalite formed is acting as an oxidizing agent, producing ketone and hydrogen halides, which is the catalyst for ketal formation. While not wishing to be bound by any particular theory, it is our view that the following is occurring:

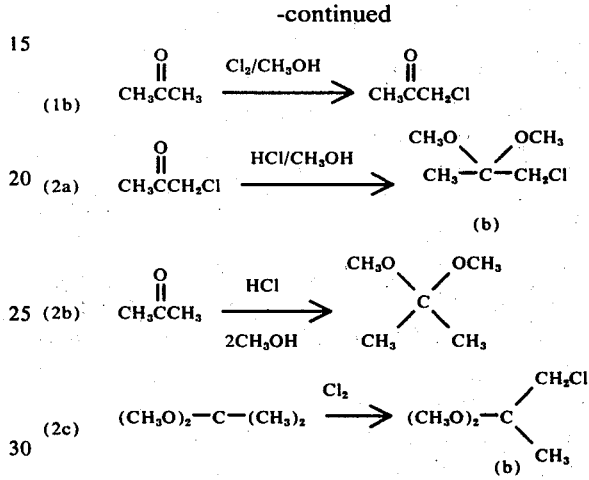

The acetone of (1b) and (2b) is formed in the initial reaction step. Further (2a) and (2b) are competing reactions taking place in the same vessel.

NOTE: "2 moles of halogen are required in order to insure that the secondary alcohol formed as a result of the cleavage is oxidized to the ketone".

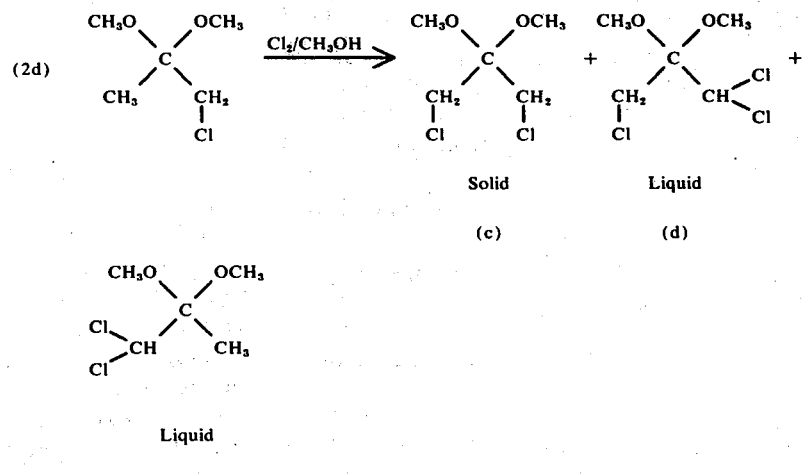

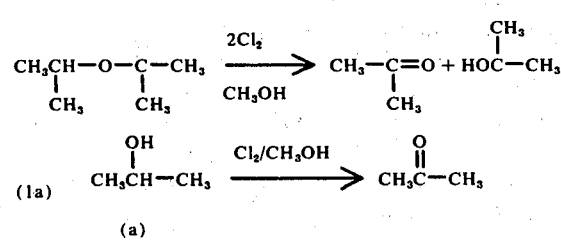

c. can be separated by crystallization at −70° C.

The initial oxidation produces its own catalyst so that reactions (2a) and (2b) can occur.

The symmetrically formed dichloro ketal differs from the unsymmetrically formed one in that chlorination stops at the symmetrical stage while the unsymmetrical, e.g.

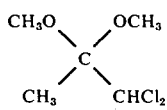

can be chlorinated further to yield, e.g.

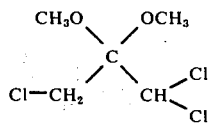

Reference has been made previously to the fact that the instant process is both selective and symmetrical.

The selectivity aspect of the invention is manifested after the cleavage step in which the secondary alcohol is formed. The halogenation then takes place only at the carbon atoms alpha to the carbinol (C-OH) group (note the reaction scheme above). It is, of course, this secondary alcohol that is oxidized to the ketone and subsequently halogenated in accordance with the above mentioned reaction scheme. This selectivity will persist regardless of the length of the alkyl portions of the formed secondary alcohol.

It is our belief, although not intending to be bound by such, that both the selectivity and degree of halogenation obtained by the instant invention are due to steric hindrance. Steric hindrance, of course, is the nonoccurrence of an expected chemical reaction, due to inhibition by a particular atomic grouping. The steric hindrance is present, initially, in the ketal itself by virtue of the alkoxy groups present in the compound. This steric hindrance causes the reaction to take place at the alkyl portion of the molecule. Thus, when the first halogen substitution takes place the ketal that is formed in the initial stages of the reaction results in a sterically hindered moiety, e.g.

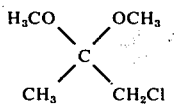

(b)     (a)

By virtue of such steric hindrance the next halogen substitution will occur primarily at (b).

As aforestated, it is believed that halogenation acid, viz., HCl or HBr, a known catalyst for ketal formation, is produced in the halogenation step. Stated otherwise, the initial halogenation step produces its own catalyst for the production of the monohalogenated ketal that ultimately results in high yields of symmetrically dihalogenated ketals. It is also reasonable to conclude that in view of the considerable amount of alcohol used, stable hypohalites as well as the hydrohalogen are also formed, which are contributing to the initial halogenation as the primary halogenating agent.

Typically secondary ethers that may be used in the instant invention cover a broad spectrum. They may be selected from the following compounds: methylisopropyl ether, diisopropyl ether, methyl-2-hexyl ether, and the like. In general, as aforestated, the secondary alkyl moiety of the ether may contain up to about 20 carbon atoms in accordance with Formula I.

The solvent media may be selected from the mono and polyhydric alcohols.

While we do not wish to be bound by any particular mechanism, it is our view that the use of methanol or any alcohol containing only C-H groups to which the -OH groups are attached prevents the ketal from decomposing into a ketone and the respective alcohol. It appears that the use of the above-mentioned type of alcohols shifts the equilibrium to the right. This prevention of decomposition of ketal is accomplished by insuring that there is an excess of the alcohol as compared to the ketal, said ratio being from about 5:1 to about 20:1, preferably about 10:1, most preferably about 5:1 in favor of the alcohol. The use of an excess of alcohol also insures the obtention of predominately selectively and symmetrically dihalogenated product. While mono and polyhydric alcohols are generally usable in the instant invention, most preferred are those wherein the alcohol contains 1-5 carbon atoms and each of the carbon atoms is hydroxylated. This includes alcohols such as methanol, ethylene glycol, glycerol, sorbitol. Alcohols higher than glycerol are generally solids, therefore it will be necessary that heat be applied to initiate the reaction.

Alcohols such as ethanol and 2,3-butanediol are within the scope of this invention, however, some oxidation of the alcohol will occur. Tolerable amounts of alcohol oxidation can readily be determined by utilizing the instant process. However, clean reactions, i.e., no alcohol oxidation, are obtained when the preferred alcohols are used.

The preferred alcohols are believed to form hypohalites which participate in the initial halogenation by providing either chloronium or bromonium ions. Additionally, it has been found that at the end of the reaction the starting alcohol is reformed from its hypohalite. This reformation is believed to occur either during or as a result of the halogenation step.

Although the invention is preferably carried out at ordinary conditions of temperature and pressure, a wide range of temperatures and pressures is contemplated, i.e., from about 0° C to about 80° C, preferably from about 20° C to about 40° C and most preferably from about 25° C to about 30° C and from about 1 to about 10 atmospheres of pressure. The proportion of chlorine or bromine used will depend upon the degree of halogenation desired. Generally the molar ratio of halogen to secondary ether will range from about 2:1 to about 5:1. The reaction should be carried out with moderate stirring accompanied by a slow introduction in order to avoid possible explosions that may be caused by high concentrations of hypohalite resulting from incomplete reactions of same with the secondary ether.

The acids used to accomplish the hydrolysis of the halogenated ketals to the halogenated ketones can be any of the conventional mineral acids such as hydrochloric, sulfuric, phosphoric, chloric, chlorous, hydrobromic, hydrofluoric, sulfurous, di and trifluoroacetic. Generally, any acid containing an electron withdrawing group may be used. The acid conditions contemplated herein are strong acid conditions, i.e., undiluted acid.

The following Examples are intended to be illustrative and in no way to be construed as limiting the invention.

EXAMPLE 1

The following reactions will illustrate the selectivity of halogenation as realized by the invention. The reaction is accomplished by simply bubbling halogen gas through an alcoholic solution of secondary ether. All the reactions are conduced in a 250 ml 3 necked flask at room temperature and atmospheric pressure accomplished by moderate agitation. The ratio of halogen to secondary ether is 1:1 molar basis and the ratio of solvent to reactant, i.e., secondary ether is about 5:1. The ensuing equations will illustrate the yield and selectivity of the instant invention.

Products are analyzed by NMR run in $CDCl_3$ containing 1% tetramethylsilane (TMS).

Methyl isopropyl ether was prepared in the following manner:

Into a 2000 ml, one neck round bottom flask was placed 1000 mls isopropanol and 12 grams of Na. After all the Na had reacted 100 mls $CH_3I$ was added and the mixture was allowed to stand for 8 hours. The first fraction was removed under vacuum (about 100 mls) and then the product was distilled off using a 12' Vigreux fractionating column, at 40°–42° C. The product contains 60:40 methyl isopropyl ether: $CH_3I$.

NMR of $CH_3I$ a singlet of 2.03.

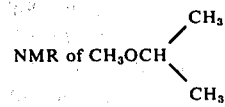

for the $CH_3$'s a doublet centered at 1.05δ
for the CH a sextet centered at 3.48δ
for the $CH_3O$ a singlet at 3.20δ

Into a 250 ml, 3 neck flask there was placed 14 grams of the above mixture and 80 mls methanol. A total of 48 grams of $Cl_2$ was bubbled through. NMR analysis showed no $CH_3I$ peak. The peaks for starting material were not present. The solution was cooled to −70° C and four grams of sym-dichloroacetone dimethyl ketal were filtered off. The filtrate consisted of a mixture of

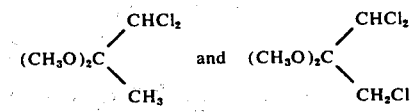

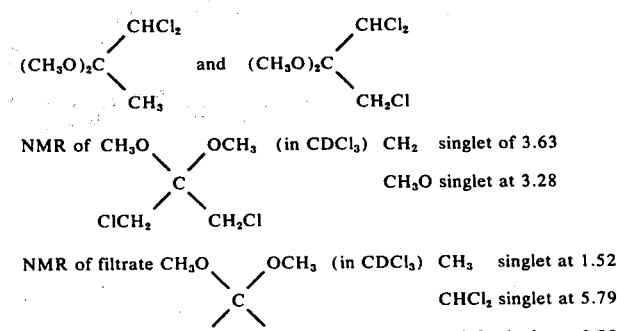

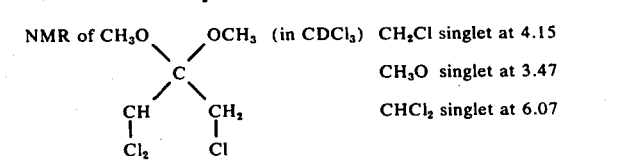

EXAMPLE 2

Into a 250 ml, 3 neck flask equipped with stirrer, inlet tube and drying tube, is placed 5.6 gram (0.05 mole)

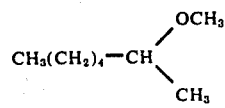

into 100 mls ethylene glycol and chlorinated slowly with 44 grams of $Cl_2$ (0.6 mole). The reaction is terminated. Diethyl ether is then added and the ether layer is washed twice with water to remove ethylene glycol. The ether layer is evaporated down, and the product is washed with water to remove

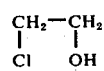

formed from reaction of $Cl_2$ with ethylene glycol. Five grams of product is obtained.

NMR of the mixture gives the following mole % ratios

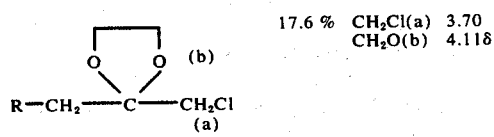

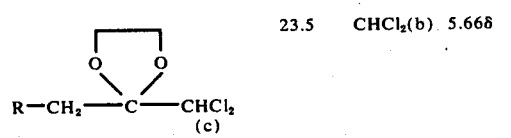

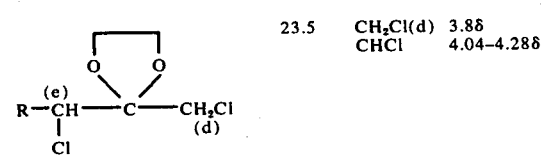

-continued

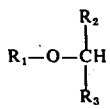

35 %   CHCl(f)  6.408
        CHCl(g)  4.7-4.928

What is claimed is:

1. A method for preparing selectively halogenated ketals which comprises treating with a halogen selected from the group consisting of chlorine and bromine ether compounds of the formula:

$$R_1-O-\underset{\underset{R_3}{|}}{\overset{\overset{R_2}{|}}{C}}H$$

wherein $R_1$ is a straight chain unsubstituted alkyl group of from 1 to 20 carbon atoms, and $R_2$ and $R_3$ are straight chain unsubstituted alkyl groups of from 1 to 10 carbon atoms; said treatment being in a polyhydric alcohol selected from the group consisting of ethylene glycol and 2,3-butanediol wherein the ratio of said alcohol to said ether is from about 5:1 to about 20:1 and at a temperature of from about 0° C to about 80° C.

2. A method according to claim 1 wherein the molar ratio of said halogen to said ether ranges from about 2:1 to about 5:1.

3. A method according to claim 1 wherein the secondary ether is selected from the group consisting of diisopropyl ether, methyl isopropyl ether, and methyl-2-hexyl ether.

4. A method according to claim 1 wherein the ratio of said alcohol to said secondary ether is from about 5:1 to about 10:1.

5. A method for preparing selectively and symmetrically dihalogenated ketals which comprises treating with a halogen selected from the group consisting of chlorine and bromine ether compounds of the formula:

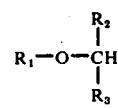

wherein $R_1$ is a straight chain unsubstituted alkyl group of from 1 to 20 carbon atoms, and $R_2$ and $R_3$ are straight chain unsubstituted alkyl groups of from 1 to 10 carbon atoms; said treatment being in a polyhydric alcohol selected from the group consisting of ethylene glycol and 2,3-butanediol wherein the ratio of said alcohol to said ether is from about 5:1 to about 20:1 and at a temperature of from about 0° C to about 80° C.

6. A method according to claim 5 wherein the molar ratio of said halogen to said ether ranges from about 2:1 to about 5:1.

7. A method according to claim 5 wherein the secondary ether is selected from the group consisting of diisopropyl ether, methyl isopropyl ether, and methyl-2-hexyl ether.

8. A method according to claim 5 wherein the ratio of said alcohol to said secondary ether is from about 5:1 to about 10:1.

* * * * *